(12) United States Patent
Skwarek et al.

(10) Patent No.: US 11,654,667 B2
(45) Date of Patent: May 23, 2023

(54) FLEXIBLE SUBSTRATES WITH CHEMICAL AND MOISTURE RESISTANCE

(71) Applicant: HONEYWELL INTERNATIONAL INC., Morris Plains, NJ (US)

(72) Inventors: Gary M. Skwarek, Kenilworth, NJ (US); Carl Altman, Pitman, PA (US); Jong Lee, Cressona, PA (US); Eric Rainal, Morristown, NJ (US); Awdhoot Vasant Kerkar, Rockaway, NJ (US); Alagappan Thenappan, Hackettstown, NJ (US)

(73) Assignee: HONEYWELL INTERNATIONAL INC., Charlotte, NC (US)

( * ) Notice: Subject to any disclaimer, the term of this patent is extended or adjusted under 35 U.S.C. 154(b) by 215 days.

(21) Appl. No.: 16/864,927

(22) Filed: May 1, 2020

(65) Prior Publication Data
US 2020/0353732 A1 Nov. 12, 2020

Related U.S. Application Data

(60) Provisional application No. 62/843,947, filed on May 6, 2019.

(51) Int. Cl.
*C08J 5/18* (2006.01)
*B32B 27/32* (2006.01)
(Continued)

(52) U.S. Cl.
CPC ............ *B32B 27/322* (2013.01); *A61K 9/703* (2013.01); *A61M 35/00* (2013.01); *B29C 48/0019* (2019.02); *B29C 48/0021* (2019.02); *B29C 48/022* (2019.02); *B29C 48/18* (2019.02); *B32B 27/08* (2013.01); *B32B 27/325* (2013.01); *B32B 27/34* (2013.01); *B32B 27/36* (2013.01); *B32B 37/153* (2013.01); *B65D 75/30* (2013.01); *A61K 9/7038* (2013.01); *A61K 9/7084* (2013.01);
(Continued)

(58) Field of Classification Search
CPC .............. B32B 27/322; B32B 2535/00; B32B 2307/7265; B32B 2307/714; B32B 2307/518; B32B 37/30; B32B 27/36; B32B 27/34; B32B 27/325; B32B 27/08; A61K 9/7038; A61M 35/00
See application file for complete search history.

(56) References Cited

U.S. PATENT DOCUMENTS 6,461,696 B1 10/2002 Ling et al.
6,538,084 B2 3/2003 Kitahara et al.
(Continued)

FOREIGN PATENT DOCUMENTS

CN 1396862 A 2/2003
CN 103052505 A 4/2013
(Continued)

*Primary Examiner* — Ellen S Hock
(74) *Attorney, Agent, or Firm* — Lorenz & Kopf, LLP

(57) ABSTRACT

Flexible packages, transdermal drug delivery devices, and methods for fabricating packages are provided. An exemplary flexible package includes a chemical and moisture resistant layer formed from poly(chlorotrifluoroethylene-co-vinylidene fluoride) ("P(CTFE-co-VDF)") copolymer. Further, the exemplary flexible package includes a substance to be delivered. The substance is applied to or enclosed by the chemical and moisture resistant layer.

20 Claims, 1 Drawing Sheet

(51) Int. Cl.
  *B32B 27/36* (2006.01)
  *B32B 27/34* (2006.01)
  *B65D 75/30* (2006.01)
  *B32B 37/15* (2006.01)
  *B29C 48/00* (2019.01)
  *B29C 48/18* (2019.01)
  *A61M 35/00* (2006.01)
  *B32B 27/08* (2006.01)
  *A61K 9/70* (2006.01)
  *B29L 31/00* (2006.01)
  *B29K 27/00* (2006.01)

(52) U.S. Cl.
  CPC ..... *B29K 2027/16* (2013.01); *B29L 2031/712* (2013.01); *B32B 2307/518* (2013.01); *B32B 2307/714* (2013.01); *B32B 2307/7265* (2013.01); *B32B 2439/40* (2013.01); *B32B 2439/80* (2013.01); *B32B 2535/00* (2013.01)

(56) References Cited

U.S. PATENT DOCUMENTS

| | | | |
|---|---|---|---|
| 7,337,593 | B2 | 3/2008 | Blum et al. |
| 8,603,272 | B2 | 12/2013 | Prejean et al. |
| 10,829,281 | B2 | 11/2020 | Idan et al. |
| 11,260,624 | B2 | 3/2022 | Christensen et al. |
| 2004/0063805 | A1 | 4/2004 | Pacetti et al. |
| 2004/0239047 | A1 | 12/2004 | Kent |
| 2007/0128393 | A1 | 6/2007 | Moulton et al. |
| 2015/0158644 | A1 | 6/2015 | Ting |
| 2018/0030225 | A1 | 2/2018 | Lee et al. |
| 2019/0002656 | A1* | 1/2019 | Liu .................... C08J 5/18 |

FOREIGN PATENT DOCUMENTS

| | | |
|---|---|---|
| CN | 107921771 A1 | 4/2018 |
| CN | 108367534 A | 8/2018 |
| EP | 1542740 B1 | 5/2009 |

* cited by examiner

FLEXIBLE SUBSTRATES WITH CHEMICAL AND MOISTURE RESISTANCE

CROSS-REFERENCE TO RELATED APPLICATION

This application claims the benefit of priority to U.S. provisional patent application Ser. No. 62/843,947, filed on May 6, 2019, titled "FLEXIBLE SUBSTRATES WITH CHEMICAL AND MOISTURE RESISTANCE", the contents of which are herein incorporated by reference in their entirety.

TECHNICAL FIELD

The technical field generally relates to packages and transdermal drug delivery devices, and to methods for fabricating such packages or devices. More particularly, the technical field relates to chemical and moisture resistant substrates in such packages and devices.

BACKGROUND

A wide variety of thermoplastic polymers, and films formed from thermoplastic polymers are known. Important physical and chemical characteristics of thermoplastic polymer films include barrier properties, such as barriers to gas, chemical resistance, aroma and moisture, as well as its physical characteristics, such as durability, toughness, wear and weathering resistances, and light-transmittance. These properties are especially important in film applications such as, for example, in the use of films as a packaging material for food, cosmetics, or medical products.

It is known in the art to produce multicomponent structures incorporating different properties exhibited by the various individual components in a single film structure. For example, in packaging applications, it is desirable to use fluoropolymers which are known for their barrier properties, inertness to most chemicals, resistance to high temperatures and low coefficients of friction. Polychlorotrifluoroethylene ("PCTFE") homopolymers and copolymers, and ethylene-chlorotrifluoroethylene ("ECTFE") alternating copolymers, have frequently been used due to their excellent moisture barrier properties.

A variety of different thermoplastics have been co-extruded with fluoropolymers to form multilayered films. For example, fluoropolymer containing multilayer films could include a layer of nylon to improve toughness, or a layer of ethylene vinyl alcohol or polyvinyl alcohol as an oxygen barrier. However, fluoropolymers do not adhere strongly to most other polymers without the aid of an adhesive layer. In fact, most fluoropolymers are known for their non-stick characteristics and suffer from poor bond strength between layers and delamination of multilayer films. Fluoropolymer films are also known to have poor heat sealability properties.

While the aforementioned materials have been useful as lidding and packaging products, there is a need for improved materials for use in flexible packaging. Further, such materials are needed to provide both improved chemical resistance and moisture resistance. Also, such materials are desirable for facilitating use in heat-sealing applications or other plastic welding technologies such as laser, radiofrequency (RF), and ultrasonic sealing.

Accordingly, it is desirable to provide flexible packages or transdermal drug delivery devices formed from a layer or layers exhibiting improved chemical and moisture resistance. Further, it is desirable to provide methods for producing flexible packages or transdermal drug delivery devices from such layers. Furthermore, other desirable features and characteristics will become apparent from the subsequent detailed description and the appended claims, taken in conjunction with the accompanying drawings and this background.

BRIEF SUMMARY

Flexible packages, transdermal drug delivery devices, and methods for fabricating packages are provided. An exemplary flexible package includes a chemical and moisture resistant layer formed from poly(chlorotrifluoroethylene-co-vinylidene fluoride) ("P(CTFE-co-VDF)") copolymer and may include fitments, connectors, closures and or tubing composed of the same materials. Further, the exemplary flexible package includes a substance to be delivered. The substance is applied to or enclosed by the chemical and moisture resistant layer.

In another exemplary embodiment, a transdermal drug delivery device is provided. The transdermal delivery device includes a chemical and moisture resistant layer comprising poly(chlorotrifluoroethylene-co-vinylidene fluoride) ("P(CTFE-co-VDF)") copolymer. The P(CTFE-co-VDF) copolymer comprises from about 0 to about 5 wt. % vinylidene fluoride ("VDF"), based on the total weight of the copolymer. Further, the transdermal drug delivery device includes a second layer releasably connected to the chemical and moisture resistant layer. Also, the transdermal drug delivery device includes a drug located between the chemical and moisture resistant layer and the second layer.

In another embodiment, a method for fabricating a package is provided. The method for fabricating a package includes providing a poly(chlorotrifluoroethylene-co-vinylidene fluoride) ("P(CTFE-co-VDF)") copolymer composition and extruding a layer of the copolymer composition. Further, the method includes forming from the layer of the copolymer composition a first segment having edges and a second segment having edges. Also, the method includes sealing the edges of the first segment to the edges of the second segment, thereby forming the package.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

The various embodiments will hereinafter be described in conjunction with the following drawing figures, wherein like numerals denote like elements, and wherein.

DETAILED DESCRIPTION

The following detailed description is merely exemplary in nature and is not intended to limit the flexible packages and transdermal drug delivery devices, or the fabrication methods. Furthermore, there is no intention to be bound by any theory presented in the preceding background or the following detailed description.

As described herein, flexible packages are provided with chemical and moisture resistant layers formed from P(CTFE-co-VDF) copolymer. An exemplary chemical and moisture resistant layer consists of P(CTFE-co-VDF) copolymer. In other embodiments, a chemical and moisture resistant layer may include P(CTFE-co-VDF) copolymer and an acrylonitrile copolymer, cyclic olefin copolymer (COC), polyethylene terephthalate (PET), foil, and/or biaxially oriented polyamide (BOPA). For example, exemplary layers may include acrylonitrile-methyl acrylate copolymer sold under the Barex® by INEOS Barex AG of Cologne, Germany. Other suitable acrylonitrile copolymers may be used. In layers utilizing both a P(CTFE-co-VDF) copolymer and an acrylonitrile copolymer, cyclic olefin copolymer (COC), polyethylene terephthalate (PET), foil, and/or biaxially oriented polyamide (BOPA), the P(CTFE-co-VDF) copolymer may be co-extruded with the other material(s) as a single layer, or may be laminated to from a laminate structure of sub-layers.

The flexible packages are further provided with a substance to be delivered, such as a drug, therapeutic, cosmetic, ointment, food, water, solvent, or other suitable substance. The substance to be delivered may be in solid, gel, liquid, fibrous, powder, or other desired form. The substance to be delivered may be applied to or enclosed by the chemical and moisture resistant layer.

An exemplary flexible package is provided as a drug delivery device and includes a drug either applied to or enclosed by the chemical and moisture resistant layer or layers. During use, the drug is exposed by separating the drug from a releasable liner, which may be formed by a chemical and moisture resistant layer of P(CTFE-co-VDF) copolymer, or by removing the drug from a pouch or enclosure formed from the chemical and moisture resistant layer of P(CTFE-co-VDF) copolymer.

Figure 1:
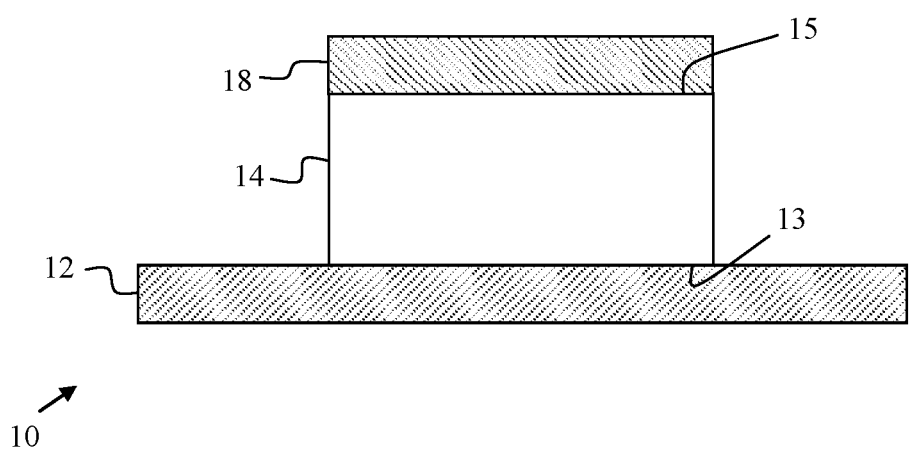
FIG. 1 illustrates a cross-section through a schematic, perspective view of a non-enclosed flexible package including a layer formed from P(CTFE-co-VDF) copolymer in accordance with an embodiment herein.

Referring to FIG. 1, an exemplary flexible package 10 is illustrated. As shown, the flexible package 10 includes a chemical and moisture resistant layer 12. Layer 12 may be considered to be a backing layer. Exemplary layer 12 is formed from poly(chlorotrifluoroethylene-co-vinylidene fluoride) ("P(CTFE-co-VDF)") copolymer. For example, layer 12 may consist of P(CTFE-co-VDF) copolymer, may be a co-extrusion of P(CTFE-co-VDF) copolymer and an acrylonitrile copolymer, cyclic olefin copolymer (COC), polyethylene terephthalate (PET), foil, and/or biaxially oriented polyamide (BOPA), or may be a laminate structure including a layer or layers of P(CTFE-co-VDF) copolymer and a layer or layers of an acrylonitrile copolymer, cyclic olefin copolymer (COC), polyethylene terephthalate (PET), foil, and/or biaxially oriented polyamide (BOPA), and/or others.

In exemplary embodiments, the P(CTFE-co-VDF) copolymer includes from about 0 to about 10 weight percent (wt. %) of vinylidene fluoride ("VDF"), such as from about 0 to about 5 weight percent (wt. %) of VDF, based on the total weight of the copolymer. For example, the P(CTFE-co-VDF) copolymer may include from about 4 to about 5 wt. % VDF, such as about 5 wt. % VDF, based on the total weight of the copolymer. Alternatively, the P(CTFE-co-VDF) copolymer may include from about 2 to about 3 wt. % VDF, such as about 2.5 wt. % VDF, based on the total weight of the copolymer. In other embodiments, the chemical and moisture resistant layer 12 may be formed by more than one P(CTFE-co-VDF) copolymer. For example, layer 12 may be formed by a P(CTFE-co-VDF) copolymer including from about 4 to about 5 wt. % VDF and from a P(CTFE-co-VDF) copolymer including from about 2 to about 3 wt. % VDF. Such embodiments may include a co-extruded layer or layers of the P(CTFE-co-VDF) copolymers or laminate structures including sublayers of each P(CTFE-co-VDF) copolymer, or laminate structures including a co-extruded layer or layers.

As shown in FIG. 1, the flexible package 10 further includes a substance to be delivered 14. In FIG. 1, the substance 14 is applied directly to the chemical and moisture resistant layer 12. For example, the substance 14 may be a matrix including a drug and an adhesive, or may be naturally adhesive such that the substance 14 is in direct contact with layer 12. In other embodiments, the flexible package 10 may be considered to include an additional adhesive layer (not shown) for adhering the substance 14 to layer 12.

In either embodiment, substance 14 has a back side 13 and a front side 15. As shown, the back side 13 of substance 14 is applied, directly or indirectly, to the chemical and moisture resistant layer 12.

As shown in FIG. 1, the package 10 may further include a second layer 18. Second layer 18 may be considered to be a releasable liner. The front side 15 of substance 14 is applied, directly or indirectly, to the second layer 18.

Second layer 18 may be compositionally identical to the chemical and moisture resistant layer 12, i.e., formed from the same copolymer composition. Alternatively, second layer 18 may be formed from a composition independent and distinct from layer 12. For example, second layer 18 may be formed from P(CTFE-co-VDF) copolymer or from P(CTFE-co-VDF) copolymer and a material selected from acrylonitrile copolymer, cyclic olefin copolymer (COC), polyethylene terephthalate (PET), foil, and/or biaxially oriented polyamide (BOPA).

The flexible package 10 may be further packaged, such as in an enclosure. For use, the flexible package 10 is removed from external packaging, and the second layer 18 is removed from the substance 14. The front side 15 of substance 14 may be applied to the ski of a user, such as for transdermal drug delivery. In other embodiments, an implement may be used to scrape or otherwise remove substance 14 from layer 12. Likewise, layer 12 may be handled to apply substance 14 to another article.

Figure 2:
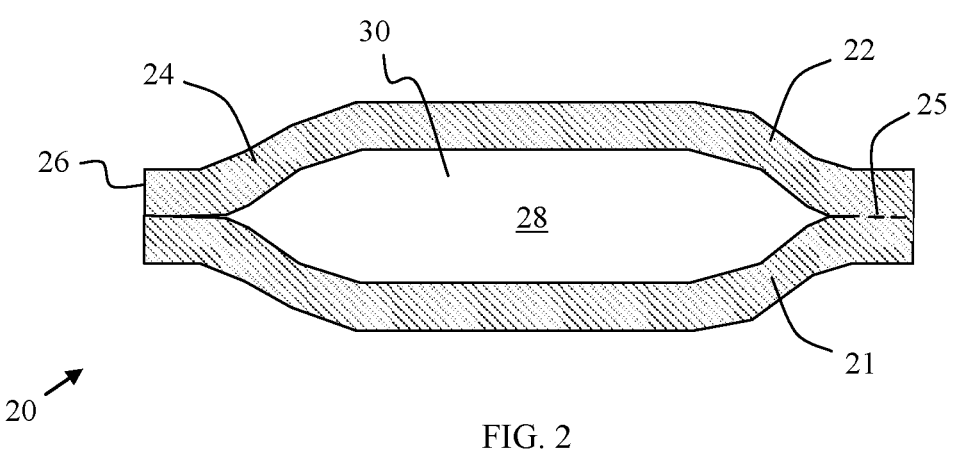
FIG. 2 illustrates a cross-section through a schematic, perspective view of a non-enclosed flexible package including a layer formed from P(CTFE-co-VDF) copolymer in accordance with an embodiment herein.

FIG. 2 illustrates another embodiment of a flexible package 20 in the form of a pouch. In FIG. 2, the flexible package 20 includes a chemical and moisture resistant layer 26. Exemplary layer 26 is formed from poly(chlorotrifluoroethylene-co-vinylidene fluoride) ("P(CTFE-co-VDF)") copolymer. For example, layer 26 may consist of P(CTFE-co-VDF) copolymer, may be a co-extrusion of P(CTFE-co-VDF) copolymer and an acrylonitrile copolymer, cyclic olefin copolymer (COC), polyethylene terephthalate (PET), foil, and/or biaxially oriented polyamide (BOPA), or may be a laminate structure including a layer or layers of P(CTFE-co-VDF) copolymer and a layer or layers of an acrylonitrile copolymer, cyclic olefin copolymer (COC), polyethylene terephthalate (PET), foil, and/or biaxially oriented polyamide (BOPA).

In exemplary embodiments, the P(CTFE-co-VDF) copolymer includes from about 0 to about 10 weight percent (wt. %) of vinylidene fluoride ("VDF"), such as from about 0 to about 5 weight percent (wt. %) of VDF, based on the total weight of the copolymer. For example, the P(CTFE-co-VDF) copolymer may include from about 4 to about 5 wt. % VDF, such as about 5 wt. % VDF, based on the total weight of the copolymer. Alternatively, the P(CTFE-co- VDF) copolymer may include from about 2 to about 3 wt. % VDF, such as about 2.5 wt. % VDF, based on the total weight of the copolymer. In other embodiments, the chemical and moisture resistant layer 26 may be formed by more than one P(CTFE-co-VDF) copolymer. For example, layer 26 may be formed by a P(CTFE-co-VDF) copolymer including from about 4 to about 5 wt. % VDF and from a P(CTFE-co-VDF) copolymer including from about 2 to about 3 wt. % VDF. Such embodiments may include a co-extruded layer or layers of the P(CTFE-co-VDF) copolymers or laminate structures including sublayers of each P(CTFE-co-VDF) copolymer, or laminate structures including a co-extruded layer or layers.

As shown in FIG. 2, layer 26 includes a first segment 21 and a second segment 22. The first segment 21 may be considered to be a first layer of at least one P(CTFE-co-VDF) copolymer and the second segment 22 may be considered to be a second layer of at least one P(CTFE-co-VDF) copolymer. In certain embodiments, the first segment 21 and second segment 22 may be unitary. For example, the first segment 21 and second segment 22 may be formed from a common sheet by folding the sheet at a fold 25.

Whether unitary or not, the first segment 21 and second segment 22 are bounded by edges 26. As shown in FIG. 2, the edges 26 of the first segment 21 are sealed to the edges 26 of the second segment 22. For example, the edges 26 of the segments 21 and 22 are heat sealed together.

By joining the edges 26 of the segments 21 and 22 an enclosure or completely enclosed cavity 28 is defined between the segments 21 and 22. As shown, a substance to be delivered 30 is located in the enclosed cavity 28. In certain embodiments, a package 10 as described in FIG. 1 may be located in the enclosed cavity 28.

In other embodiments, substance 30 may be a drug, therapeutic, cosmetic, ointment, or food in solid, gel, liquid, fibrous, or powder form. In certain embodiments, substance 30 may be a liquid that is injected into or otherwise located in the enclosed cavity 28. Substance 30 may be positioned between segments 21 and 22 before or after the sealing process, provided that the cavity 28 may be re-sealed if pierced to fill the cavity 30.

In certain embodiments of FIG. 2, the substance 30 may be considered to be applied directly to the chemical and moisture resistant layer 28, as no intermediary adhesive or other material is necessary.

The P(CTFE-co-VDF) copolymer described above for use in the embodiments of FIGS. 1 and 2 may be formed via either suspension or emulsion polymerization processes. P(CTFE-co-VDF) copolymer compositions having from about 0 wt. % to about 10% wt. % of the VDF moiety, from which the packages and devices are formed may be polymerized by conventional free-radical polymerization methods. Any suitable commercially available radical initiator may be used in the process. Suitable candidates may include thermal initiators and oxidation-reduction or "redox" initiator systems. Thermal initiators include: metal persulfates such as potassium persulfate and ammonium persulfate; organic peroxides or hydroperoxides such as diacyl peroxides, ketone peroxides, peroxyesters, dialkyl peroxides and peroxy ketals; azo initiators such as 2,2'-azobisisobutyronitrile and water-soluble analogues thereof and mixtures and combinations thereof.

Generally, any redox initiator system known to be useful in the preparation of fluoropolymers such as P(CTFE-co-VDF) may be used. Typical redox initiator systems comprise: 1) an organic or inorganic oxidizing agent or mixtures thereof and 2) an organic or inorganic reducing agent or mixtures thereof. Suitable oxidizing agents include metal persulfates such as potassium persulfate and ammonium persulfate; peroxides such as hydrogen peroxide, potassium peroxide, ammonium peroxide, tertiary butyl hydroperoxide ("TBHP") (($CH_3)_3COOH$)), cumene hydroperoxide, and t-amyl hydroperoxide; manganese triacetate; potassium permanganate; ascorbic acid and mixtures thereof. Suitable reducing agents include sodium sulfites such as sodium bisulfite, sodium sulfite, sodium pyrosulfite, sodium-m-bisulfite ("MBS") ($Na_2S_2O_5$) and sodium thiosulfate; other sulfites such as ammonium bisulfite; hydroxylamine; hydrazine; ferrous irons; organic acids such as oxalic acid, malonic acid, citric acid and combinations thereof.

An exemplary free radical initiating system serves to simultaneously emulsify the polymer while initiating the polymerization, thus eliminating the need for large quantities of surfactants. Redox initiator systems may be preferred radical initiators. Suitable redox initiator systems may use an MBS reducing agent and a TBHP oxidizing agent. In an exemplary embodiment, the redox initiator system is used in conjunction with a transition metal accelerator. Accelerators can greatly reduce the polymerization time. Any commercially available suitable transition metal may be used as an accelerator, including copper, silver, titanium, ferrous iron and mixtures thereof.

The amount of radical initiator used in the process may depend on the relative ease with which the various monomers copolymerize, the molecular weight of the polymer and the rate of reaction desired. Generally, from about 10 to about 100,000 ppm of initiator may be used, such as from about 100 to about 10,000 ppm.

Optionally, in order to further accelerate the polymerization, the redox initiator system may include additional peroxide-based compounds. The amount of additional peroxide-based compound used may be from about 10 to about 10,000 ppm, such as from about 100 to about 5,000 ppm. The radical initiator may be added before, simultaneous with and/or shortly after the addition and/or consumption of the monomers used to make the copolymer. When an additional peroxide-based compound is used it may be added at the same interval specified for the primary radical initiator.

In an exemplary process for the preparation of the P(CTFE-co-VDF) copolymer includes a polymerization reaction in which monomers, water and a initial charge of radical initiator are introduced into suitable polymerization vessel. Additional monomer is added throughout the reaction at a rate equal to the rate of consumption to maintain a constant pressure. Incremental additional charges of initiator are introduced into the vessel over the duration of the reaction to sustain the polymerization. The reaction mixture is maintained at a controlled temperature while all reactants are being charged to the vessel and throughout the polymerization reaction.

The only requirement for the reaction vessel used to prepare the P(CTFE-CO-VDF) copolymer is that it be capable of being pressurized and agitated. The process may utilize conventional commercial autoclaves that can be sealed and pressurized to the required reaction pressures (such as less than 3.36 MPa (500 psig) for safety considerations). In certain embodiments, the reactor vessel is lined with a fluoropolymer or glass liner.

In exemplary embodiments, the aqueous medium in which the polymerization is conducted may be deionized, nitrogen-purged water. Generally, an amount equivalent to approximately half the capacity of the autoclave is used. The ratio of polymer to water is chosen in such a way to obtain a dispersion of about 20 to about 60% polymer solids in water. The water is pre-charged to the autoclave.

In exemplary embodiments, the monomers may be charged to the reactor vessel either in a semicontinuous or a continuous manner during the course of the polymerization. "Semicontinuous" means that a number of batches of the monomers are charged to the reactor during the course of the polymerization reaction.

The molar ratio of total monomer consumed to radical initiator will depend upon the molecular weight desired. Preferably, the overall mole ratio of monomer to initiator would be from about 10 to about 10,000, such as from about 50 to about 1,000, and for example from about 100 to about 500 moles of total monomer to one mole of initiator.

In exemplary embodiments, the radical initiator is generally added incrementally over the course of the reaction. For purposes of this discussion, "initial charge" or "initial charging" of initiator refers to a rapid, large, single or incremental addition of initiator to cause the onset of polymerization. In the initial charge, generally between about 10 ppm/min to about 1,000 ppm/min is added over a period of from about 3 to about 30 minutes, either before, after, or during the charging of the monomers. "Continuous charge" or "continuous charging" means the slow, small, incremental addition of initiator over a period of from about 1 hour to about 6 hours, or until polymerization has concluded. In the continuous charge, generally between about 0.1 ppm/min to about 30 ppm/min of initiator is added.

During the initiation of the polymerization reaction, the sealed reactor and its contents are maintained at the desired reaction temperature, or alternately to a varying temperature profile which varies the temperature during the course of the reaction. Control of the reaction temperature is another important factor for establishing the final molecular weight of the copolymers produced. As a general rule, polymerization temperature is inversely proportional to product molecular weight. Typically, the reaction temperature should be from about 0° C. to about 150° C., although temperatures above and below these values are also contemplated. The reaction pressure may be from about 172 KPa to about 5.5 MPa, such as from about 345 KPa to about 4.2 MPa. Elevated pressures and temperatures will yield greater reaction rates.

In exemplary embodiments, the polymerization is conducted under agitation to ensure proper mixing. Although the agitation rate and reaction time will typically depend upon the amount of copolymer product desired, one of ordinary skill in the art can readily optimize the conditions of the reaction without undue experimentation. The agitation rate will generally be in the range of from about 5 to about 800 rpm, such as from about 25 to about 700 rpm, depending on the geometry of the agitator and the size of the vessel. The reaction time will generally be from about 1 to about 24 hours, such as from about 1 to about 8 hours.

Dispersions prepared using a surfactant-free emulsion process obtain stable dispersions having up to 40 wt. % solids in water, which is obtained without a concentration step. Low levels of surfactants may be added to obtain higher levels of emulsified polymer in water (i.e., from about 40 to about 60 wt. %). Suitable surfactants will readily occur to those skilled in the art and include anionic, cationic and nonionic surfactants. An exemplary dispersion is an anionic surfactant stabilized latex emulsion having from about 0 to about 0.25 wt. % of an anionic emulsifier.

Exemplary surfactants are perfluorinated anionic surfactants. Examples of suitable perfluorinated anionic surfactants include perfluorinated ammonium octanoate, perfluorinated alkyl/aryl ammonium (metal) carboxylates and perfluorinated alkyl/aryl lithium (metal) sulfonates wherein the alkyl group has from about 1 to about 20 carbon atoms. Suitable surfactants also include fluorinated ionic or nonionic surfactants, hydrocarbon-based surfactants such as the alkylbenzenesulfonates or mixtures of any of the foregoing.

The copolymers produced by the above process may be isolated by conventional methods such as evaporating the water medium, freeze-drying the aqueous suspension, or adding a minor amount of an agglomerating or coagulating agent such as ammonium carbonate, followed by filtration or centrifuging. Alternatively, the copolymer dispersion produced may be used as is.

Depending upon the application desired, other components may also be included, such as wetting and leveling agents such as octylphenoxypolyethoxyethanol; pigments such as titanium dioxide; thickeners such as hydrophobe modified alkali swellable emulsions (HEURASE); defoamers; UV absorbers; plasticizers such as butyl benzylphthalate; biocides; fillers such as glass beads, as well as nanospheres; stain resists such as aqueous PTFE or fine powder PTFE; and the like.

The exemplary layer 12 or 26 may be formed as a monolayer film of P(CTFE-co-VDF) copolymer using well known extrusion techniques. In other embodiments, layer 12 or 26 may include the P(CTFE-co-VDF) copolymer layer or layers, the acrylonitrile copolymer, cyclic olefin copolymer (COC), polyethylene terephthalate (PET), foil, and/or biaxially oriented polyamide (BOPA) layer or layers, and any other layers attached to each other by co-extrusion.

For co-extrusions, the polymeric materials for the individual layers are fed into infeed hoppers of a like number of extruders, each extruder handling the material for one or more of the layers. The melted and plasticated streams from the individual extruders may be fed into a single manifold co-extrusion die. While in the die, the layers may be juxtaposed and combined, and then emerge from the die as a single multiple layer film of polymeric material. After exiting the die, the film is cast onto a first controlled temperature casting roll, passes around the first roll, and then onto a second controlled temperature roll, which is normally cooler than the first roll. The controlled temperature rolls largely control the rate of cooling of the film after it exits the die. Additional rolls may be employed. In another method, the film forming apparatus may be one which is referred to in the art as a blown film apparatus and includes a multi-manifold circular die head for bubble blown film through which the plasticized film composition is forced and formed into a film bubble which may ultimately be collapsed and formed into a film. Processes of co-extrusion to form film and sheet laminates are generally known.

Alternatively individual sub-layers may first be formed as separate layers and then laminated together under heat and pressure to form a laminate structure. Lamination techniques are well known in the art. Typically, laminating is done by positioning the individual layers on one another under conditions of sufficient heat and pressure to cause the layers to combine into a unitary film. The individual layers may be positioned on one another and the combination passed through the nip of a pair of heated laminating rollers by techniques well known in the art. Typically, lamination may be conducted with or without intermediate adhesive layers. In an exemplary embodiment, no intermediate adhesive layer is used in between the copolymer layers. Lamination heating may be done at temperatures of from about 120° C. to about 225° C., such as from about 150° C. to about 175° C., and at pressures from about 5 psig (0.034 MPa) to about 100 psig (0.69 MPa), for from about 5 seconds to about 5 minutes, such as from about 30 seconds to about 1 minute.

Each layer may be oriented prior to being joined. The term draw ratio is an indication of the increase in the dimension in the direction of draw. In certain embodiments, the layers are drawn to a draw ratio of from 1.5:1 to 5:1 uniaxially in at least one direction, i.e., the longitudinal direction, the transverse direction or biaxially in each of the longitudinal and transverse directions. The layers may be simultaneously biaxially oriented, for example orienting a plasticized film in both the machine and transverse directions at the same time. This results in dramatic improvements in clarity strength and toughness properties. The layers may be biaxially oriented and not heat set so that the layers are shrinkable both in transverse and longitudinal directions. Alternately, a multi-layer film may be uniaxially or biaxially oriented as a whole after joining the individual film layers.

Although each layer of a film structure may have a different thickness, the thickness of the copolymer layer or layers may be from about 8 μm to about 254 μm, such as from about 8 μm to about 102 μm, for example from about 8 μm to about 13 μm. The thickness of the acrylonitrile copolymer, cyclic olefin copolymer (COC), polyethylene terephthalate (PET), foil, and/or biaxially oriented polyamide (BOPA) layer or layers, if present, may be from about 1 μm to about 250 μm, such as from about 5 μm to about 225 μm, for example from about 10 μm to about 200 μm. Accordingly, the overall film thickness may be from about 9 μm to about 504 μm, such as from about 13 μm to about 327 μm, for example from about 18 μm to about 213 μm. While such thicknesses are disclosed, it is to be understood that other film thicknesses may be produced to satisfy a particular need and yet fall within the scope of the subject matter.

The water vapor transmission rate (WVTR) of the heat sealable packages, devices and layers may be determined via the procedure set forth in ASTM F1249. In an exemplary embodiment, the packages, devices and layers have a WVTR of from about 0.0005 to about 1 gm/100 in$^2$/day of the overall article at 37.8° C. and 100% RH, such as from about 0.001 to about 0.1 gm/100 in$^2$/day of the overall article, for example from about 0.003 to about 0.05 gm/100 in$^2$/day of the overall article. As is well known in the art, the water vapor transmission rate is directly influenced by the thickness of the individual film layers as well as by the overall film thickness.

The exemplary heat sealable layers are heat shrinkable, generally by an amount of from about 2% to about 30%, such as from about 10% to about 20% in length, or width, or each of length and width. The layers may further have printed indicia on or between layers. Such printing is typically on an internal surface of the structure and methods of application are well known in the art.

As described above, exemplary layers are useful for forming packages by sealing portions of the layer to itself. For example, a single layer of copolymer or copolymers may be extruded or co-extruded, folded and positioned such that the layer is overlaid onto itself forming an overlap having a top edge and side edges, and sealing together the side edges and optionally the top edge to form a package. The sealing process may be performed by a heat-sealing application or by other plastic welding technologies such as laser, radiofrequency (RF), and ultrasonic sealing. Heat sealing techniques are well known in the art, and involve the application heat to melt and fuse portions of the polymer layer together at temperatures ranging from about 150° C. to about 270° C., such as from about 200° C. to about 250° C., and pressures of from about 10 psia to about 100 psia, such as from about 60 psi to about 100 psi. The heat seal process forms a strong interlayer bond between copolymer film surfaces that has the same moisture barrier properties as the parent copolymer material, avoiding the need for an adhesive tie layer and overcoming the typical reduction in moisture barrier properties associated with low moisture barrier adhesive materials.

According to embodiments herein, the flexible package is able to withstand gamma irradiation processing and/or cryogenic processing.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the subject matter in any way. Rather, the foregoing detailed description will provide those skilled in the art with a convenient road map for implementing an exemplary embodiment. It being understood that various changes may be made in the function and arrangement of elements described in an exemplary embodiment without departing from the scope as set forth in the appended claims.

What is claimed is:

1. A transdermal drug delivery device comprising:
   a chemical and moisture resistant layer comprising poly(chlorotrifluoroethylene-co-vinylidene fluoride) ("P(CTFE-co-VDF)") copolymer, wherein the P(CTFE-co-VDF) copolymer comprises no more than about 5 wt. % vinylidene fluoride ("VDF"), based on the total weight of the copolymer, wherein the chemical and moisture resistant layer has a first side and a second side;
   a second layer releasably connected to the second side of the chemical and moisture resistant layer; and
   a drug located between the second side of the chemical and moisture resistant layer and the second layer,
   wherein the first side of the chemical and moisture resistant layer forms an outermost surface of the transdermal drug delivery device.

2. The transdermal drug delivery device of claim 1 wherein the chemical and moisture resistant layer comprises a co-extrusion of P(CTFE-co-VDF) copolymer and an acrylonitrile copolymer, cyclic olefin copolymer (COC), polyethylene terephthalate (PET), foil, and/or biaxially oriented polyamide (BOPA).

3. The transdermal drug delivery device of claim 1 wherein the chemical and moisture resistant layer comprises a laminate structure including a layer of P(CTFE-co-VDF) copolymer and a layer of an acrylonitrile copolymer, cyclic olefin copolymer (COC), polyethylene terephthalate (PET), foil, and/or biaxially oriented polyamide (BOPA).

4. The transdermal drug delivery device of claim 1 wherein the drug is dispersed in a matrix, and wherein the matrix directly contacts the chemical and moisture resistant layer and the second layer.

5. The transdermal drug delivery device of claim 1 wherein the second layer comprises P(CTFE-co-VDF) copolymer, wherein the P(CTFE-co-VDF) copolymer comprises no more than about 5 wt. % vinylidene fluoride (VDF), based on the total weight of the copolymer.

6. The transdermal drug delivery device of claim 1 wherein no material layer is interposed between the drug and the second side of the chemical and moisture resistant layer.

7. The transdermal drug delivery device of claim 1 wherein the drug is dispersed in a matrix, wherein the matrix has a front side and a back side, wherein the front side is in direct contact with the second layer, and wherein all of the back side is in direct contact with the second side of the chemical and moisture resistant layer.

8. The transdermal drug delivery device of claim 1 wherein the drug is dispersed in a matrix, wherein the matrix has a front side and a back side, and wherein no material layer is interposed between the back side and the second side of the chemical and moisture resistant layer.

9. The transdermal drug delivery device of claim 1 wherein the second layer is releasably connected to the second side of the chemical and moisture resistant layer by the drug located between the second side of the chemical and moisture resistant layer and the second layer.

10. The transdermal drug delivery device of claim 1 wherein the second layer is releasably connected to the second side of the chemical and moisture resistant layer by the drug located between the second side of the chemical and moisture resistant layer and the second layer, and wherein the transdermal drug delivery device consists of the chemical and moisture resistant layer, the drug, and the second layer.

11. The transdermal drug delivery device of claim 1 wherein the transdermal drug delivery device consists of the chemical and moisture resistant layer, the drug, and the second layer.

12. The transdermal drug delivery device of claim 1 further comprising an adhesive for adhering the drug to the chemical and moisture resistant layer, wherein the transdermal drug delivery device consists of the chemical and moisture resistant layer, the drug, the second layer, and the adhesive.

13. The transdermal drug delivery device of claim 2 wherein the chemical and moisture resistant layer comprises a co-extrusion of P(CTFE-co-VDF) copolymer and an acrylonitrile copolymer.

14. The transdermal drug delivery device of claim 2 wherein the chemical and moisture resistant layer comprises a co-extrusion of P(CTFE-co-VDF) copolymer and a cyclic olefin copolymer (COC).

15. The transdermal drug delivery device of claim 2 wherein the chemical and moisture resistant layer comprises a co-extrusion of P(CTFE-co-VDF) copolymer and a polyethylene terephthalate (PET).

16. The transdermal drug delivery device of claim 2 wherein the chemical and moisture resistant layer comprises a co-extrusion of P(CTFE-co-VDF) copolymer and a foil.

17. The transdermal drug delivery device of claim 2 wherein the chemical and moisture resistant layer comprises a co-extrusion of P(CTFE-co-VDF) copolymer and a biaxially oriented polyamide (BOPA).

18. The transdermal drug delivery device of claim 3 wherein the chemical and moisture resistant layer comprises a laminate structure including a layer of P(CTFE-co-VDF) copolymer and a layer of a cyclic olefin copolymer (COC), polyethylene terephthalate (PET), and/or biaxially oriented polyamide (BOPA).

19. A transdermal drug delivery device comprising:
a chemical and moisture resistant layer comprising poly (chlorotrifluoroethylene-co-vinylidene fluoride) ("P (CTFE-co-VDF)") copolymer, wherein the P(CTFE-co-VDF) copolymer comprises no more than about 5 wt. % vinylidene fluoride ("VDF"), based on the total weight of the copolymer, wherein the chemical and moisture resistant layer has a first side and a second side;
a second layer releasably connected to the second side of the chemical and moisture resistant layer; and
a drug located between the second side of the chemical and moisture resistant layer and the second layer, wherein the drug is dispersed in a matrix, wherein the matrix has a back side extending from a first edge to a second edge, and wherein the back side is in continuous contact with the chemical and moisture resistant layer from the first edge to the second edge.

20. A transdermal drug delivery device consisting of:
a chemical and moisture resistant layer comprising poly (chlorotrifluoroethylene-co-vinylidene fluoride) ("P (CTFE-co-VDF)") copolymer, wherein the P(CTFE-co-VDF) copolymer comprises no more than about 5 wt. % vinylidene fluoride ("VDF"), based on the total weight of the copolymer, wherein the chemical and moisture resistant layer has a first side and a second side;
a second layer releasably connected to the second side of the chemical and moisture resistant layer; and
a drug located between the second side of the chemical and moisture resistant layer and the second layer.

\* \* \* \* \*